United States Patent [19]

Hachmann et al.

[11] Patent Number: 5,403,505
[45] Date of Patent: Apr. 4, 1995

[54] CLEANING AND DISINFECTING AGENT CONTAINING AN N-SUBSTITUTED PROPYLENE GLUTAMIC ACID OR DERIVATIVE THEREOF, AND AN ANTIMICROBIALLY ACTIVE COMPOUND

[75] Inventors: Klaus Hachmann, Hilden; Karlheinz Disch, Haan; Klaus-Peter Bansemir, Langenfeld; Hubert Schwidden, Duesseldorf; Stephanie Kaupp, Böblingen; Carsten Friese, Hilden; Rudolf Lehmann, Leichlingen; Hans T. Leinen, Duesseldorf, all of Germany

[73] Assignee: Henkel Kommanditgesellschaft auf Aktien, Duesseldorf, Germany

[21] Appl. No.: 923,969

[22] PCT Filed: Mar. 4, 1991

[86] PCT No.: PCT/EP91/00400
§ 371 Date: Nov. 12, 1992
§ 102(e) Date: Nov. 12, 1992

[87] PCT Pub. No.: WO91/13965
PCT Pub. Date: Sep. 19, 1991

[30] Foreign Application Priority Data
Mar. 12, 1990 [DE] Germany .................. 40 07 758.6

[51] Int. Cl.⁶ ............................................. C11D 3/48
[52] U.S. Cl. .................................... 252/106; 252/134; 422/16; 514/563
[58] Field of Search ............... 252/106, 134; 422/16; 514/563

[56] References Cited
U.S. PATENT DOCUMENTS

| | | | |
|---|---|---|---|
| 4,336,270 | 6/1982 | Montwyler | 252/8.6 |
| 4,584,121 | 4/1986 | Blaschke et al. | 252/106 |
| 4,652,585 | 3/1987 | Gerhardt et al. | 514/563 |
| 5,000,867 | 3/1991 | Heinhus-Walther et al. | 252/106 |

Primary Examiner—Paul Lieberman
Assistant Examiner—Necholus Ogden
Attorney, Agent, or Firm—Ernest G. Szoke; Wayne C. Jaeschke; Henry E. Millson, Jr.

[57] ABSTRACT

An aqueous cleaning and disinfecting concentrate comprising
A) at lease one reaction product of
 a) an N-substituted propylene diamine of formula I $$R^1—NH—(CH_2)_3—NH_2 \qquad (I)$$

in which $R^1$ is a $C_8$-$C_{18}$ alkyl group and
 b) glutamic acid or a glutamic acid derivative of formula II $$R_2—O—CO—(CH_2)_2—CH(NH_2)—COOH \qquad (II)$$

in which $R^2$ is hydrogen or a $C_1$-$C_4$ alkyl group, wherein the said reaction product is optionally ethoxylated and/or propoxylated, and is optionally in the form of a salt with an organic or inorganic acid;
B) at least one of the following antimicrobially active compounds:
 i) a quaternary ammonium compound of formula III $$\begin{array}{c} R^3 \\ | \\ R^4—N^+—R^6 \quad X^- \\ | \\ R^5 \end{array} \qquad (III)$$

in which $R^3$ and $R^4$ independently of one another represent alkyl radicals containing 1 to 3 carbon atoms or benzyl radicals, or halogenated or alkylated benzyl radicals containing 6 to 22 carbon atoms, and $X^-$ is an anion;
 ii) a phenol;
 iii) a biguanide;
 (iv) a quaternary phosphonium compound of formula IV (Abstract continued on next page.)"

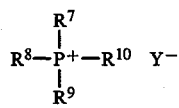

in which $R^7$, $R^8$, $R^9$ and $R^{10}$ are each independently an alkyl, alkenyl, aryl, or alkaryl group having from 1 to 16 carbon atoms, and $Y^-$ is an anion; and C) at least one low foaming surfactant.

The invention also relates to the diluted concentrates, and to the method of use of the diluted concentrates, especially for the disinfection of medical equipment.

20 Claims, No Drawings

CLEANING AND DISINFECTING AGENT CONTAINING AN N-SUBSTITUTED PROPYLENE GLUTAMIC ACID OR DERIVATIVE THEREOF, AND AN ANTIMICROBIALLY ACTIVE COMPOUND

This invention relates to a preparation for cleaning and disinfecting items of medical equipment and to a process using this preparation in an automatic machine for the spray cleaning and spray disinfection of items of medical equipment.

Automatic program-controlled washing machines are normally used in hospitals for cleaning and disinfecting items of equipment, for example bedsteads. These machines consist essentially of a closed chamber in which the articles to be cleaned are sprayed with one or more cleaning and/or disinfecting solutions which generally have elevated temperatures of normally above 50° C. In machines of the type in question, the cleaning and disinfecting solutions, which are normally prepared by dissolving solid or liquid concentrates in water and diluting the solution to the required in-use concentration, are normally accommodated in heated storage tanks and are automatically pumped through nozzles into the cleaning chamber. The contact time of the individual solutions on the articles to be cleaned and disinfected is relatively short and is generally of the order of 30 seconds to three minutes. A distinction is drawn between washing machines in which the washing solutions are repeatedly used on the circulation principle and so-called freshwater machines which use freshly prepared washing solutions for each article to be cleaned, i.e. the washing solutions are discarded after being used only once and have to be disposed of.

In freshwater systems, the articles to be disinfected are cleaned by spraying with a normally heated cleaning solution, are then optionally rinsed by spraying with water to which a rinse aid may have been added, are subsequently disinfected by spraying with a disinfectant and, in a final step, are dried. In systems of this type, the cleaning and disinfecting steps are separated from one another in time and follow one another immediately through the use of spray solutions containing different ingredients or are separated from one another by an intermediate clear rinse step.

By contrast, circulation systems use the washing solution repeatedly over a prolonged period, generally one day, so that several units to be cleaned, normally more than 100, can be cleaned with the same solution. Since only one solution is generally used in circulation systems, it must have both a cleaning and a disinfecting effect. If the machines operating on the circulation principle incorporate a clear rinse step, the clear rinse solution used in this step is either discarded after use or enters the circulating cleaning solution which is thus increasingly diluted, so that particularly stringent demands are imposed on the cleaning and disinfecting effect of the preparation used in the wash liquor. In cases where used cleaning solution and clear rinse solution are combined with one another, part of the dilute cleaning solution normally flows off automatically according to the filling level of the storage tank and may then be replaced by optionally automatic introduction of fresh water and/or concentrated cleaning preparation.

To be able to be used in the automatic machines described above, more particularly those operating on the circulation principle, a cleaning and disinfecting preparation has to meet a number of requirements. Thus, it has to combine a good cleaning effect with a good disinfecting effect and, in addition, must be able to develop both effects in a short time. Since the liquor is sprayed under high pressure at elevated temperature in automatic machines, it must be substantially foam-free and must not be corrosive towards any of the materials processed in the articles to be cleaned. In addition, it must be compatible with the constituents of any rinse aid used which, particularly in circulation systems, can continuously enter the cleaning liquor. The in-use solution of the preparation must be stable over prolonged periods of at least one day at relatively high temperatures of at least 50° C., in addition to which the preparation should be ecologically safe both in use and for subsequent disposal.

The cleaning and disinfectant preparations hitherto used, particularly for circulation systems, normally have an acidic pH value, generally contain disinfectants with volatile constituents, for example from the class of aliphatic aldehydes, and do not fully satisfy the requirements which a cleaning and disinfecting preparation for automatic machines is expected to meet because their use can lead to odor emissions through the waste air of the cleaning machine, particularly at elevated temperatures.

Accordingly, the problem addressed by the present invention was to provide microbiologically active spray cleaning and disinfecting preparations which would be stable for prolonged periods at elevated temperature, would have a substantially neutral pH value, would be substantially non-corrosive and ecologically safe and would be foam-free under the described in-use conditions.

The cleaning preparations according to the invention, which contain a binary disinfectant combination, preferably of certain glutamic acid derivatives and quaternary ammonium compounds, one or more low-foaming surfactants, preferably from the groups of nonionic surfactants and amphoteric surfactants, and optionally one or more complexing agents, more particularly from the group of phosphonocarboxylic and aminocarboxylic acids, and/or other disinfectants, preferably from the class of quaternary phosphonium compounds, and also one or more organic solvents, more particularly from the groups of lower alcohols, glycols and glycol ethers, are foam-free under in-use conditions, stable for prolonged periods, microbiologically active, pH-neutral and non-corrosive and convincingly satisfy the requirements which cleaning and disinfecting preparations for automatic spray cleaning and spray disinfection, more particularly using machines operating on the circulation principle, are expected to satisfy.

The cleaning and disinfecting preparations according to the invention are concentrates which give solutions suitable for use in automatic spray cleaning systems by dissolution in water and dilution to the required in-use concentration, which is preferably between 0.5 and 2% by weight of cleaning preparation.

The quantities and quantitative ranges in % by weight mentioned in the following are based on the cleaning and disinfecting preparation as a whole, unless otherwise indicated.

The preparations according to the invention preferably contain a binary combination of antimicrobial agents A and B. Agent A is selected from the products obtainable by the process described in European patent EP 156 275 which comprises reacting an N-substituted propylenediamine corresponding to formula (I)

in which $R^1$ is an alkyl radical containing 8 to 18 carbon atoms and preferably 12 to 14 carbon atoms, with glutamic acid or glutamic acid derivatives corresponding to formula (II)

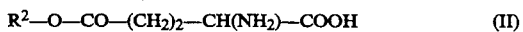

in which $R^2$ is hydrogen or a $C_{1-4}$ alkyl radical, the molar ratio of reactants (I) and (II) being 1:1 to 1:2 and the reaction being carried out with elimination of water and/or alcohol over a period of 30 minutes to 10 hours at temperatures of 60° to 175° C. These products may optionally be ethoxylated and/or propoxylated and may have been reacted with organic or inorganic acids to form salts.

The N-substituted propylenediamines corresponding to formula (I) may be produced by the method described in DE-AS 12 72 927. The production of glutamic acid-5-esters corresponding to formula (II) is described, for example, in DE-ASS 21 58 562 and 12 54 635 and in DE-OS 14 93 991.

The antimicrobial agent B is selected from quaternary ammonium compounds corresponding to formula (III)

in which $R^3$ and $R^4$ independently of one another represent alkyl radicals containing 1 to 3 carbon atoms or benzyl radicals, halogenated or alkylated benzyl radicals, $R^5$ and $R^6$ independently of one another represent alkyl or benzyl radicals, halogenated or alkylated benzyl radicals containing 6 to 22 carbon atoms and $X^-$ is an anion, preferably from the groups of halides or carboxylates. Examples are dimethyl dioctyl ammonium chloride, didecyl dimethyl ammonium chloride, didodecyl dimethyl ammonium chloride, dimethyl ditetradecyl ammonium chloride, dihexadecyl dimethyl ammonium chloride, dimethyl dioctadecyl ammonium chloride, decyl dimethyl octyl ammonium chloride, dimethyl dodecyl octyl ammonium chloride, benzyl decyl dimethyl ammonium chloride, benzyl dimethyl dodecyl ammonium chloride, benzyl dimethyl tetradecyl ammonium chloride, decyl dimethyl (ethylbenzyl) ammonium chloride, decyl dimethyl(dimethyl benzyl)-ammonium chloride, (chlorobenzyl)-decyl dimethyl ammonium chloride, decyl-(dichlorobenzyl)-dimethyl ammonium chloride, benzyl didecyl methyl ammonium chloride, benzyl didocyl methyl ammonium chloride, benzyl ditetradecyl methyl ammonium chloride, benzyl dodecyl ethyl methyl ammonium chloride and the corresponding compounds which, instead of chloride, contain acetate or propionate as anions.

However, agent A may also be combined with one of the antimicrobial agents C and, to further enhance their antimicrobial activity, the preferred disinfectant combinations A and B according to the invention may contain other antimicrobial agents C, such as quaternary phosphonium compounds, phenols or biguanide compounds, but not aldehydes. The antimicrobial agents C include, for example, o-phenylphenol, p-chloro-m-cresol, 2,4-dichlorophenol, tetra(hexamethylene biguanide hydrochloride) and 1,1'-hexamethylene-bis-5-(4-chlorophenyl biguanide). Preferred antimicrobial agents are the compounds selected from the group of quaternary phosphonium compounds corresponding to formula (IV)

in which $R^7$, $R^8$, $R^9$ and $R^{10}$ independently of one another represent alkyl, alkenyl, aryl or alkylaryl radicals containing 1 to 16 carbon atoms and $Y^-$ is an anion, preferably from the groups of halides and carboxylates, more particularly acetate or propionate. Hexadecyl tributyl phosphonium chloride and tetradecyl tributyl phosphonium chloride are particularly suitable.

The antimicrobial agents A, B and/or C are preferably used in the cleaning preparations according to the invention in ratios by weight of A to B of 8:1 to 1:8 and in ratios by weight of A to C of no lower than 1:4. The total quantity of antimicrobial agents in the cleaning preparations according to the invention is preferably from 0.5% by weight to 15% by weight and more preferably from 1% by weight to 10% by weight.

The cleaning and disinfecting preparation according to the invention also contain one or more low-foaming surfactants, preferably from the groups of nonionic surfactants and amphoteric surfactants. Suitable nonionic surfactants are alkyl glycosides containing $C_{8-22}$ alkyl components, reaction products of 4 to 20 mol equivalents ethylene oxide and/or propylene oxide with fatty alcohols, fatty acids, fatty amines, of which the fatty alkyl radicals preferably contain 8 to 22 carbon atoms, and with alkylphenols. The end-capped derivatives of these alkoxylation products, preferably those terminated by $C_{2-10}$ groups, are also suitable. Nonionic surfactants such as these include, for example, the commercial products Dehypon ® LS 24, LS 36, LS 45, LS 54, LT 24, LT 104, OCP 502 (Henkel KGaA), Dehydol ® LT 30 (Henkel KGaA), Lutensol ® LF 224, LT 30 (BASF), Triton ® CF 54 and DF 12 (Rohm & Haas). Suitable amphoteric surfactants include derivatives of tertiary aliphatic amines or quaternary aliphatic ammonium compounds of which the aliphatic radicals may be linear or branched and one of which bears a carboxy, sulfo, phosphono, sulfato or phosphato group. Examples of such amphoteric surfactants are dimethyl tetradecyl glycine, dimethyl hexadecyl glycine, dimethyl octadecyl glycine, 3-(dimethyldodecyl-ammonio)-1-propanesulfonate and the amphoteric surfactants marketed under the names of Dehyton ® AB, CB and G (Henkel KGaA).

To obtain good cleaning results under in-use conditions, the surfactants are preferably present in the preparations according to the invention in quantities of 2% by weight to 15% by weight and, more preferably, in quantities of 4% by weight to 10% by weight.

The cleaning and disinfecting preparations according to the invention may also contain water-soluble organic solvents, preferably from the groups of $C_{1-4}$ alcohols, $C_{2-4}$ glycols and the diglycols and diglycol ethers derivable therefrom. Examples of such solvents are methanol, ethanol, propanol, isopropanol, tert. butanol, ethylene glycol, propylene glycol, butylene glycol, diethylene glycol, dipropylene glycol, diethylene glycol monomethyl ether, diethylene glycol monoethyl ether, diethylene glycol monopropyl ether and diethylene glycol monobutyl ether. Organic solvents are preferably present in the preparations according to the invention in quantities of no more than 35% by weight and, more preferably, in quantities of 10% by weight to 30% by weight.

To guarantee good corrosion behavior, even where the concentrated cleaning preparations according to the invention are used with hard water, the cleaning and disinfecting preparations according to the invention may contain complexing agents. The complexing agents are preferably selected from the groups of phosphonic acids, hydroxyphosphonic acids, aminophosphonic acids, phosphonocarboxylic acids, aminocarboxylic acids and salts thereof, more particularly alkali metal salts. Suitable complexing agents are, for example, methane diphosphonic acid, hydroxyethane-1,1-diphosphonic acid, 1-aminoethane-1,1-diphosphonic acid, aminotri(methylene phosphonic acid), ethylenediamine tetra(methylene phosphonic acid), diethylenetriamine penta(methylene phosphonic acid), 2-phosphonobutane-1,2,4-tricarboxylic acid, nitrilotriacetic acid, ethylenediamine tetraacetic acid and hydroxyethyl ethylenediamine triacetic acid. Corrosion inhibitors such as these are present in the preparations according to the invention in quantities of preferably not more than 6% by weight and, more particularly, in quantities of 1% by weight to 5% by weight.

In addition, the concentrated cleaning and disinfecting preparations according to the invention may contain typical additives, such as dyes, corrosion inhibitors or fragrances. These typical additives are preferably present in the preparations according to the invention in quantities of not more than 1% by weight.

The cleaning preparations according to the invention preferably contain the individual components in the following quantities:
  0.5 to 15% by weight antimicrobial agents
  2 to 15% by weight surfactant,
  0 to 35% by weight organic solvent,
  0 to 6% by weight complexing agent,
  0 to 1% by weight typical additives.

Water-based cleaning preparations containing the individual components in the following quantities are particularly preferred:
  0.5 to 4.0% by weight antimicrobial agent A,
  0.5 to 4.0% by weight antimicrobial agent B,
  0 to 2.0% by weight antimicrobial agent C,
  4 to 10% by weight surfactant.
  10 to 30% by weight organic solvent,
  1 to 5% by weight complexing agent,
  0 to 0.5% by weight typical additives.

Unless they have a substantially neutral pH value of preferably 6.5 to 7.5 through the nature of their constituents, the concentrated cleaning and disinfecting preparations according to the invention may be adjusted to pH values in that range by addition of small quantities of typical acids or bases compatible with the other ingredients, including in particular citric acid and sodium hydroxide.

The production of the cleaning preparations according to the invention does not present any problems. In the most simple case, it is carried out by mixing of the components which may be used either in bulk or in the form of aqueous solutions. The cleaning and disinfecting preparation according to the invention may be used as such or preferably diluted with water, more particularly in concentrations of 0.5% by weight to 2% by weight, for disinfecting instruments and for cleaning and disinfecting hard surfaces. It is used with particular advantage in processes carried out in automatic cleaning machines. The process preferably comprises the steps of a) spraying on an aqueous disinfecting cleaning solution at elevated temperature, preferably in the range from 50° C. to 80° C., which has been prepared by dilution of the concentrate according to the invention with water, preferably to concentrations of 0.5% by weight to 2% by weight; if desired, b) spraying on an aqueous, optionally surfactant-containing clear rinse solution and, optionally, c) drying, for example with hot air. A particularly preferred embodiment of the cleaning process comprises returning the used cleaning solution optionally diluted with the clear rinse solution to a storage tank and reusing the solution to which fresh cleaning and disinfecting concentrate may be added—optionally automatically —beforehand.

EXAMPLES

Example 1

A clear, storable cleaning and disinfecting preparation (B1) having the following composition (balance to 100% by weight) was prepared by combining and mixing the individual constituents:
  3% by weight glutamic derivative[a]
  1% by weight dimethyl didecyl ammonium propionate
  0.6% by weight tributyl tetradecyl phosphonium chloride
  7% by weight propoxylated $C_{12/14}$ fatty alkyl ethoxylate (Dehypon ® LS, a product of Henkel KGaA)
  2% by weight diethylene glycol monobutyl ether
  1.5% by weight 2-phosphonobutane-1,2,4-tricarboxylic acid
  3% by weight trisodium nitrilotriacetate
  30% by weight isopropanol In undiluted form, it had a pH value of 6.9 and, in concentrations of 1.0% by weight or 0.5% by weight in tapwater, a pH value of 7.0.

[a] Product of the reaction of glutamic acid with N—$C_{12/14}$-fatty alkyl propylenediamine (molar ratio 1:1 ) with elimination of 1 tool equivalent water (EP 156 275)

Example 2

Practical test

Preparation B1 was tested for its disinfecting effect in an automatic bedwashing machine (manufacturer: Münchener Medizin Mechanik) in accordance with the "Richtlinie des Bundesgesundheitsamtes zur Prüfung yon thermischen Desinfektionsverfahren in Reinigungsautomaten (Directive of the Federal Health Office for the Testing of Thermal Disinfection Processes in Automatic Cleaning Machines" (Bundesgesundheitsblatt 23 (1980), 364–367) and the "Richtlinien der Deutschen Gesellschaft für Hygiene und Mikrobiologie für die Prüfung und Bewertung chemischer Desinfektionsverfahren (Guidelines of the DGHM for the Testing and Evaluation of Chemical Disinfection Processes)" (Zbl. Bakt. Hyg., I. Abt. Orig. B 165.( 1977), 335). The tests were carried out on hospital beds with flat mattresses, a plastic-coated metal frame and head and foot parts of Resopal ® with a matt surface. *Streptococcus faecalis* ATTC 6057 with controlled heat resistance (70° C./10 minutes) was used as the test germ while defibrinated rams' blood (Oxoid) and artificial sputum of mucin (Difco), tragacanth (Merck) and bovine serum (Oxoid) were used as the carrier media. The germ density in the carrier media was $4.4 \cdot 10^8$ per milliliter (blood) and $3.8 \cdot 10^8$ per milliliter (artifical sputum). Resopal ® plates (15 cm $\times$ 15 cm $\times$ 1.5 mm) with a matt surface and stainless steel plates (8 cm $\times$ 8 cm $\times$ 1.5 mm) with a polished surface were used for contamination, test zones measuring 5 cm $\times$ 5 cm being marked thereon with water-resistant dye. With the aid of sterile swabs, each test zone was provided with a uniform layer of approx. 0.2 ml test soil which was then left to dry for 24 hours. Using transparent adhesive tape, the test plates were fastened at all their edges to the hospital beds described above in such a way that one plate of each test material and each test soil was present at the head and foot parts both on the outside and on the inside. Accordingly, each bed was contaminated with a total of 16 test zones.

The beds were cleaned with circulating water (temperature 65° C.) containing 1.5% by weight of cleaning preparation B1, empty runs being made before the beginning of the test (5 beds) and between the individual test beds (1 to 3 beds in each case). Between two test beds, 5 ml rams' blood was added to the storage tank for the cleaning liquor. After each test bed, one sample and, after the 5th bed, two samples (100 ml each) were taken from the cleaning liquor and, after addition of 100 ml of a concentrated nutrient broth (Merck) and incubation (14 days at 37° C.), were microbiologically investigated (Table 3).

The contact time of the cleaning solution on the contaminated beds was 90 seconds or 60 seconds (Tables 1 and 2) and was followed by clear rinsing for 30 seconds with a 0.05% by weight aqueous solution of a pH-neutral wetting agent of alkoxylated fatty alcohols (Dehypon ® LS 54, a product of Henkel KGaA), the clear rinse solution entering the circulated cleaning solution, and then by drying (180 seconds).

TABLE 1

| | | I | | II | | III | | IV | |
|---|---|---|---|---|---|---|---|---|---|
| | | S | R | S | R | S | R | S | R |
| NP | CT | a b | a b | a b | a b | a b | a b | a b | a b |
| 6 | 90 | — — | — — | — — | — — | — — | — — | — — | — — |
| 10 | 90 | + + | — — | — — | — — | — — | — — | — — | — — |
| 14 | 90 | + — | — + | — + | — — | — — | — — | — — | — — |
| 18 | 90 | — — | — — | — — | — — | nd | — — | nd | — — |
| 21 | 90 | nd | — — | nd | — — | nd | — — | nd | — — |
| 24 | 60 | — — | — — | — + | — — | — — | — — | — — | — — |
| 26 | 60 | — — | — — | — — | — — | — — | — — | — — | — — |
| 28 | 60 | — — | — — | — — | — — | — — | — — | — — | — — |
| 30 | 60 | — — | — — | — — | — — | nd | — — | nd | — — |
| 32 | 60 | nd | — — | nd | — — | nd | — — | nd | — — |

(Germ carrier blood)

TABLE 2

(Germ carrier artificial sputum)

| | | I | | II | | III | | IV | |
|---|---|---|---|---|---|---|---|---|---|
| | | S | R | S | R | S | R | S | R |
| NP | CT | a b | a b | a b | a b | a b | a b | a b | a b |
| 6 | 90 | — — | — — | — — | — — | — — | — — | — — | — — |
| 10 | 90 | — — | — — | — — | — — | — — | — — | — — | — — |
| 14 | 90 | — — | — — | — — | — — | — — | — — | — — | — — |
| 18 | 90 | — — | — + | — — | — — | nd | — — | nd | — — |
| 21 | 90 | nd | — — | nd | — — | nd | — — | nd | — — |
| 24 | 60 | — — | — — | — — | — — | — — | — — | — — | — — |
| 26 | 60 | — — | — — | — — | — — | — — | — — | — — | — — |
| 28 | 60 | — — | — — | — — | — — | — — | — — | — — | — — |
| 30 | 60 | — — | — — | — — | — — | nd | — — | nd | — — |
| 32 | 60 | nd | — — | nd | — — | nd | — — | nd | — — |

TABLE 2-continued (Germ carrier artificial sputum)

Legends to Tables 1 and 2:
NP: number of passes
CT: contact time [seconds]
S: test surface of stainless steel
R: test surface of Resopal ®
I: test surface fixed to outside of head part
II: test surface fixed to inside of head part
III: test surface fixed to outside of foot part
IV: test surface fixed to inside of foot part
a: sampling with Rodac ® plates
b: sampling with swabs
nd: determination not carried out Before and after cleaning, samples were taken from the individual test zones with sterile swabs or with Rodac ® plates from which samples were in turn taken with sterile swabs, the swabs were spread out onto solid nutrient media and, after incubation for 72 hours at 37° C., the nutrient media were examined by microscope for the test germ used.

Before the beginning of the test, the test germs could be detected in all samples of all test zones (lawn-like growth on the nutrient media). After machine cleaning and disinfection, all test zones were optically clean. In six test zones, a spray shadow with residual contamination could be seen under the transparent adhesive tape. With seven exceptions, no germs could be detected on the washed test zones (Tables 1 and 2). The test germ could not be re-isolated from the samples of cleaning liquor (Table 3).

TABLE 3

| Microbiological investigation of the cleaning liquor | | |
|---|---|---|
| Sample after bed No. | Growth in sample 1 | Growth in sample 2 |
| 1 | — | Spb |
| 2 | — | — |
| 3 | — | — |
| 4 | — | nd |
| 5 | — | nd |
| 6 | — | nd |
| 7 | — | nd |
| 8 | — | — |
| 9 | Spb | — |
| 10 | — | — |

Legend to Table 3:
-: no aerobic growth
Spb: aerobic spore formers
nd: determination not carried out

We claim:
1. An aqueous cleaning and disinfecting concentrate comprising
A) at least one reaction product of
a) an N-substituted propylene diamine of formula I

$$R^1-NH-(CH_2)_3-NH_2 \qquad (I)$$

in which $R^1$ is a $C_8$-$C_{18}$ alkyl group and
b) glutamic acid or a glutamic acid derivative of formula II $$R_2-O-CO-(CH_2)_2-CH(NH_2)-COOH \qquad (II)$$

in which $R_2$ is hydrogen or a $C_1$–$C_4$ alkyl group, wherein the said reaction product is optionally ethoxylated or propoxylated, or ethoxylated and propoxylated and is optionally in the form of a salt with an organic or inorganic acid;

B) at least one of the following antimicrobially active compounds:
(i) a quaternary ammonium compound of formula III

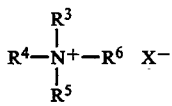

in which $R^3$ and $R^4$ independently of one another represent alkyl radicals containing 1 to 3 carbon atoms or benzyl radicals or halogenated or alkylated benzyl radicals, $R^3$ and $R^4$ independently of one another represent alkyl or benzyl radicals or halogenated or alkylated benzyl radicals containing 6 to 22 carbon atoms, and x is a anion;
(ii) a phenol;
(iii) a biguanide;
(iv) a quaternary phosphonium compound of formula IV

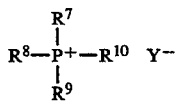

in which $R^7$, $R^8$, $R^9$ and $R^{10}$ are each independently an alkyl, alkenyl, aryl, or alkaryl group having from 1 to 16 carbon atoms, and $Y^-$ is an anion; and C) at least one low foaming surfactant.

2. The concentrate of claim 1 wherein component A) and component B)i) are present in a ratio by weight of from about 8:1 to about 1:8.

3. The concentrate of claim 1 wherein component A) and component B)ii), iii), and/or iv) are present in a ratio by weight of component A) to component B) of not less than about 1:4.

4. The concentrate of claim 1 wherein components B)i) and B)iv) are both present therein.

5. The concentrate of claim 1 wherein component C) is a nonionic tenside and/or an amphoteric tenside.

6. The concentrate of claim 1 wherein the concentrate also contains a complexing agent.

7. The concentrate of claim 6 wherein the complexing agent is at least one of a phosphonic acid, a hydroxyphosphonic acid, a phosphonocarboxylic acid, an aminocarboxylic acid, an aminophosphonic acid, and a salt of any of the foregoing.

8. The concentrate of claim 1 wherein the concentrate also contains a water-soluble organic solvent.

9. The concentrate of claim 8 wherein the water-soluble organic solvent is at least one of a $C_1$–$C_4$ alkanol, a $C_2$–$C_4$ glycol, and a diglycol or diglycol ether derived from the foregoing.

10. The concentrate of claim 1 wherein the concentrate has a pH in the range of from about 6.5 to about 7.5, or is adjusted with an acid or base to a pH in the above range.

11. The concentrate of claim 1 wherein in component A) $R^1$ is a $C_{12}$–$C_{14}$ alkyl group.

12. The concentrate of claim 1 wherein in component B)i) $X^-$ is a halide or a carboxylate anion.

13. The concentrate of claim 1 wherein in component B)iv) $Y^-$ is a halide or a carboxylate anion.

14. The concentrate of claim 1 containing the following:
from about 0.5 to about 15% by weight of component A) plus component B);
from about 2 to about 15% by weight of component C);
from about 0 to about 35% by weight of a water-soluble organic solvent;
from about 0 to about 6% by weight of a complexing agent; and
from about 0 to about 1% by weight of other additives.

15. The concentrate of claim 13 which contains
from about 0.5 to about 4.0% by weight of component A);
from about 0.5 to about 4.0% by weight of component B)i);
from 0 to about 2.0% by weight of component B)ii), iii, and/or iv);
from about 4 to about 10% by weight of component C);
from about 10 to about 30% by weight of water-soluble organic solvent;
from about 1 to about 5% by weight of complexing agent; and
from 0 to about 0.5% by weight of other additives.

16. The concentrate of claim 15 wherein in component A) $R^1$ is a $C_{12}$–$C_{14}$ alkyl group, components B)i) and B)iv) are both present therein, component C) is a nonionic tenside and/or an amphoteric tenside, the water-soluble organic solvent is at least one of a $C_1$–$C_4$ alkanol, a $C_2$–$C_4$ glycol, and a diglycol or diglycol ether derived from the foregoing, the complexing agent is at least one of a phosphonic acid, a hydroxyphosphonic acid, a phosphonocarboxylic acid, an aminocarboxylic acid, an aminophosphonic acid, and a salt of any of the foregoing, and wherein the concentrate has a pH in the range of from about 6.5 to about 7.5, or is adjusted with an acid or base to a pH in the above range.

17. An aqueous cleaning and disinfecting solution containing from about 0.5. to about 2% by weight of the concentrate of claim 1.

18. An aqueous cleaning and disinfecting solution containing from about 0.5 to about 2% by weight of the concentrate of claim 15.

19. A process for cleaning and disinfecting hard surfaces comprising contacting the hard surface with the solution of claim 17 at a temperature in the range of from about 50° to about 80° C.

20. A process for cleaning and disinfecting hard surfaces comprising contacting the hard surface with the solution of claim 18 at a temperature in the range of from about 50° to about 80° C.

* * * * *